United States Patent
Edwards et al.

(10) Patent No.: US 7,881,493 B1
(45) Date of Patent: Feb. 1, 2011

(54) METHODS AND APPARATUSES FOR USE OF EYE INTERPRETATION INFORMATION

(75) Inventors: Gregory T. Edwards, Roseville, CA (US); Colin Johnson, San Francisco, CA (US)

(73) Assignee: Eyetools, Inc., Roseville, CA (US)

( * ) Notice: Subject to any disclaimer, the term of this patent is extended or adjusted under 35 U.S.C. 154(b) by 716 days.

(21) Appl. No.: 10/821,800

(22) Filed: Apr. 9, 2004

Related U.S. Application Data

(60) Provisional application No. 60/462,045, filed on Apr. 11, 2003.

(51) Int. Cl.
  G06K 9/00  (2006.01)
  A61B 3/14  (2006.01)
  A61B 13/00 (2006.01)
  H04N 7/18  (2006.01)

(52) U.S. Cl. .................. 382/103; 351/209; 600/558; 348/78

(58) Field of Classification Search .......... 382/103, 382/117; 351/209; 348/78; 600/558
See application file for complete search history.

(56) References Cited

U.S. PATENT DOCUMENTS

| | | | |
|---|---|---|---|
| 5,844,824 A * | 12/1998 | Newman et al. ............ 345/156 |
| 5,886,683 A * | 3/1999 | Tognazzini et al. ......... 715/700 |
| 6,090,051 A | 7/2000 | Marshall |
| 6,102,870 A * | 8/2000 | Edwards .................... 600/558 |
| 6,106,119 A * | 8/2000 | Edwards .................... 351/209 |
| 6,359,601 B1 | 3/2002 | Maguire, Jr. |
| 6,405,159 B2 | 6/2002 | Bushey et al. |
| 6,433,760 B1 | 8/2002 | Vaissie et al. |
| 6,601,021 B2 * | 7/2003 | Card et al. ................. 702/187 |
| 6,608,615 B1 * | 8/2003 | Martins ..................... 345/156 |
| 6,697,818 B2 | 2/2004 | Li et al. |
| 6,755,527 B1 * | 6/2004 | Goldberg ................... 351/209 |
| 6,778,150 B1 | 8/2004 | Maguire, Jr. |
| RE38,668 E | 12/2004 | Edwards |
| 2003/0122839 A1 * | 7/2003 | Matraszek et al. .......... 345/581 |
| 2005/0108092 A1 | 5/2005 | Campbell et al. |
| 2006/0161144 A1 | 7/2006 | Li |
| 2007/0040799 A1 | 2/2007 | Singh et al. |
| 2007/0066916 A1 | 3/2007 | Lemos |

FOREIGN PATENT DOCUMENTS

WO  WO0225637 A1 *  3/2002

OTHER PUBLICATIONS

Hatfield et al., Nov. 30, 1997, "An Interface integrating eye gaze and voice recognition for hands-free computer access" (pp. 1-7).*

(Continued)

*Primary Examiner*—Manav Seth
(74) *Attorney, Agent, or Firm*—Blakely Sokoloff Taylor & Zafman

(57) ABSTRACT

Eyetracking techniques and analysis techniques are disclosed. At least one interpretation of eyetracking data is received from an eye interpretation engine. A characteristic of an application is dynamically modified based on the interpretation of the eyetracking data. A portion of the application being viewed by a user may be determined. The determined portion may be modified in response to the interpretation of the eyetracking data for the user.

19 Claims, 15 Drawing Sheets

OTHER PUBLICATIONS

Privitera et al., 2000, "Algorithms for defining visual-of-interest:comparison with eye fixations" (pp. 970-982).*

Hatfield et al., 1995, "Eye/Voice mission planning interface (EVMPI)".*

Office Action for U.S. Appl. No. 11/584,382 mailed Sep. 16, 2008, 12 pgs.

Office Action for U.S. Appl. No. 11/584,382 mailed Oct. 5, 2009, 11 pgs.

Edwards, Gregory T., et al., "Method and Apparatuses for Use of Eye Interpretation Information", U.S. Appl. No. 10/821,800, filed Apr. 6, 2004.

Edwards, Gregory T., et al., "Methods and Apparatuses for Collection, Processing, and Utilization of Viewing Data", U.S. Appl. No. 11/584,382, filed Oct. 19, 2006.

Johnson, Colin, et al., "Evaluation of Visual Stimuli Using Existing Viewing Data", U.S. Appl. No. 11/638,133, filed Dec. 12, 2006.

Final Office Action for U.S. Appl. No. 11/584,382 mailed Mar. 19, 2009, Whole Document.

* cited by examiner

METHODS AND APPARATUSES FOR USE OF EYE INTERPRETATION INFORMATION

RELATED APPLICATIONS

This U.S. patent application claims priority to provisional application No. 60/462,045, filed Apr. 11, 2003, entitled "EYE INTERPRETATION ENGINES AND RELATED METHODS AND APPARATUSES."

TECHNICAL FIELD

The invention relates to eye tracking. More particularly, the invention relates to techniques and applications for use in association with eye interpretation engines.

BACKGROUND

Devices currently exist that can track the movement of a person's face and eyes as that person engages in an activity, for example, using a computer system, or while in a car, or as a person walks around in the world. Eye tracking devices generally consist of a camera and associated electronic components to produce data representing gaze positions (or "gaze data"). This gaze data can be used to determine where the individual is looking, which can be described in terms of fixations (a steady gaze for a predetermined period of time) and saccades (movement of the gaze between two points).

When the gaze data is combined with data representing graphical or visual images presented to the user, the combined data indicates what the person was viewing (or "viewing data"). The viewing data can be used, for example, to determine whether a viewer has looked at all of the information presented. The viewing data is typically presented graphically as a series of circles and lines indicating the fixations and saccades, respectively.

BRIEF DESCRIPTION OF THE DRAWINGS

The invention is illustrated by way of example, and not by way of limitation, in the figures of the accompanying drawings in which like reference numerals refer to similar elements.

DETAILED DESCRIPTION

Techniques for using eye tracking data using eye interpretation engines are described. In the following description, for purposes of explanation, numerous specific details are set forth in order to provide a thorough understanding of the invention. It will be apparent, however, to one skilled in the art that the invention can be practiced without some of these specific details. In other instances, structures and devices are shown in block diagram form in order to avoid obscuring the invention.

Brief Glossary

In the description that follows, the following definitions are used:

Eyetracker: Any method, device or technique for measuring and reporting where an individual, group, or other entity is looking in 2, 3, 4 or more dimensions.

Eyetracker Data: Data returned by an eyetracker, which can include for one eye, two eyes, or a combination of the eyes' data, for example, x-axis, y-axis and/or z-axis coordinates, time, pupil diameter, percent of eyelid open, object(s) being viewed on a computer screen or in the world or an environment (reported explicitly or implicitly via the coordinate system), distance from eye(s) to the point or object being viewed, extent of peripheral vision, and/or other eye-related data.

Eye Interpretation Engine (EIE): Any technique, algorithm embodied in computer-readable instructions, circuit and/or device capable of computing higher-level characteristics and/or behaviors from eyetracking data from one or more people, with or without additional environmental data or supporting context. EIEs can also add data to the eyetracking data such as probable field of peripheral vision for an individual or a group, or related to the object being viewed if it is known, as well as other data that would be a super-set of that returned by an eyetracker. As EIEs improve, the increased functionality can be incorporated into eye-aware applications.

Application: Any technique, algorithm embodied in computer-readable instructions, circuit and/or device that receives input signals or data and generates output data or signals.

Eye-Aware Application: Any application that makes use of eyetracking data. In one embodiment, an architecture having access to an EIE or embodying an EIE that can recognize various behaviors and/or mental states can be used to provide one or more applications with improved functionality as compared to the prior art.

Example Eyetracking Architecture Capable of Recognizing Behaviors

Figure 1:
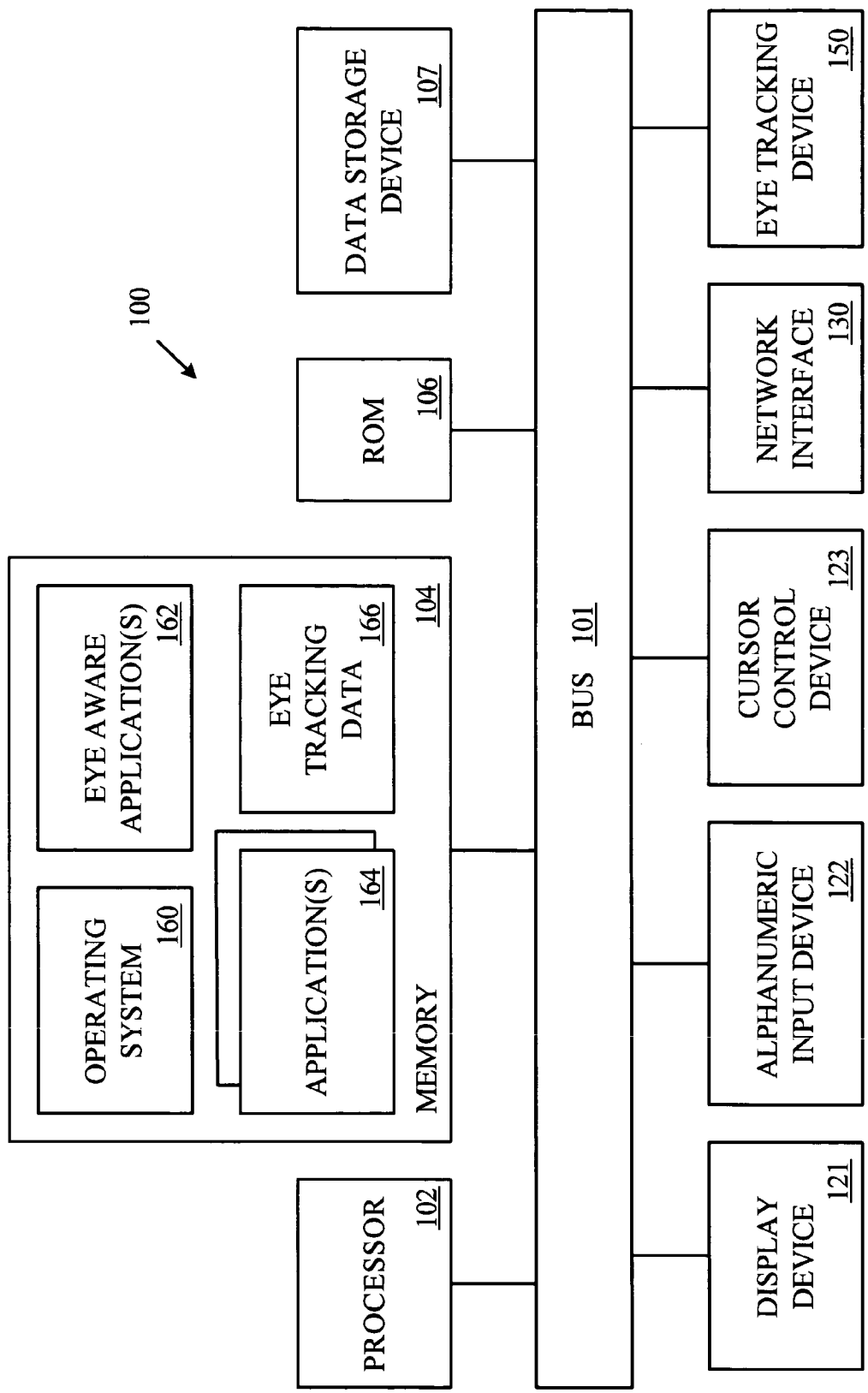
FIG. 1 is a block diagram of one embodiment of an electronic system.

FIG. 1 is a block diagram of one embodiment of an electronic system. The electronic system illustrated in FIG. 1 is intended to represent a range of electronic systems, for example, computer systems, network access devices, personal digital assistants (PDAs), etc. Alternative electronic systems can include more, fewer and/or different components.

For reasons of simplicity of description, electronic system 100 is described with an eye tracking device; however, the eye tracking device is not required to be part of the same electronic system that processes the eye tracking data. That is, the eye tracking device may be remote with respect to electronic system 100. As another example, of an alternate embodiment with respect to FIG. 1, electronic system 100 may include an eye tracking device, but eye tracking application, an eye interpretation engine or other device or application that makes use of eye tracking data from the eye tracking device may be remote with respect to electronic system 100.

Electronic system 100 includes bus 101 or other communication device to communicate information, and processor 102 coupled to bus 101 to process information. While electronic system 100 is illustrated with a single processor, electronic system 100 can include multiple processors and/or co-processors. Electronic system 100 further includes random access memory (RAM) or other dynamic storage device 104 (referred to as memory), coupled to bus 101 to store information and instructions to be executed by processor 102. Memory 104 also can be used to store temporary variables or other intermediate information during execution of instructions by processor 102.

Electronic system 100 also includes read only memory (ROM) and/or other static storage device 106 coupled to bus 101 to store static information and instructions for processor 102. Data storage device 107 is coupled to bus 101 to store information and instructions. Data storage device 107 such as a magnetic disk or optical disc and corresponding drive can be coupled to electronic system 100.

Memory 104 includes eye aware application(s) 162 that operate on eye tracking data 166 to generate output representative of viewing data. Additional eye tracking data (not shown in FIG. 1) can be stored on storage device 107 or accessed via network interface 130. Specific functionality of eye aware application(s) 162 and uses of eye tracking data 166 are described in greater detail below.

Memory 104 contains operating system 160, which directs operations of system 100. In one embodiment, operating system 160 is the highest layer of control of system 100. Applications 164 are lower layers of system control in that they direct operation within the allowable context of higher system layers. Application(s) 164 may contain user programs (e.g., word processor(s), electronic mail (e-mail) programs).

Electronic system 100 can also be coupled via bus 101 to display device 121, such as a cathode ray tube (CRT) or liquid crystal display (LCD), to display information to a computer user. Alphanumeric input device 122, including alphanumeric and other keys, is typically coupled to bus 101 to communicate information and command selections to processor 102. Another type of user input device is cursor control 123, such as a mouse, a trackball, or cursor direction keys to communicate direction information and command selections to processor 102 and to control cursor movement on display 121. Electronic system 100 further includes network interface 130 to provide access to a network, such as a local area network.

Eye tracking device 150 is coupled to bus 101 and generates eye tracking data 166 that can be stored in memory 104 and/or storage device 107. Eye tracking device 150 can be any type of eye tracking device known in the art. For example, eye tracking device 150 can track eye movement via optical, electrical, magnetic and/or other techniques.

Instructions are provided to memory from a storage device, such as magnetic disk, a read-only memory (ROM) integrated circuit, CD-ROM, DVD, via a remote connection (e.g., over a network via network interface 130) that is either wired or wireless providing access to one or more electronically-accessible media, etc. In alternative embodiments, hard-wired circuitry can be used in place of or in combination with software instructions. Thus, execution of sequences of instructions is not limited to any specific combination of hardware circuitry and software instructions.

An electronically-accessible medium includes any mechanism that provides (i.e., stores and/or transmits) content (e.g., computer executable instructions) in a form readable by an electronic device (e.g., a computer, a personal digital assistant, a cellular telephone). For example, a machine-accessible medium includes read only memory (ROM); random access memory (RAM); magnetic disk storage media; optical storage media; flash memory devices; etc.

In one embodiment, eye tracking device 150 generates raw data representing eye position and movement. In one embodiment, the raw data is transferred via bus 101 to memory 104 and stored as eyetracking data 166. In an alternate embodiment, eyetracking data 166 includes higher-order interpretations based on underlying raw eyetracking data. Processor 102 executes eye aware application(s) 162 that are responsive to eyetracking data 166.

At the lowest level, eye tracking data is interpreted to identify elementary features. Eye tracking data can be, for example, two-dimensional (x,y) eye gaze positions, three-dimensional (x,y,z) gaze positions, sample time (t), pupil diameter (d), (optionally) the object being viewed (which can be a computer screen, a face, or any object in the world), whether the eye is open or closed, and/or other related information such as biofeedback (e.g., sweat, temperature, heart rate, breathing rate) information. Gaze information can include position, duration, latency and/or other information related to a particular gaze. Elementary features that are determined from the eye tracking data can be, for example, fixations (position, time and/or duration), saccades (magnitude, direction and/or velocity), smoother pursuit motion (path taken by eye, velocity), blinks (duration).

In one embodiment, a fixation is defined as a statistically significant clustering of raw eye tracker data within some space-time interval. A fixation may be identified by analyzing the raw eye tracker data stream to determine if most of the eye positions during a predetermined minimum fixation time interval are within a predetermined minimum fixation space interval. For example, the raw eye tracker data stream can be analyzed to determine whether at least 80% of the eye positions during a 100 ms time interval are within a 0.25 degree space interval. Other values can also be used and other techniques can be used to identify a fixation. Many techniques are known in the art and other techniques for identifying fixations can be used.

A saccade can be defined as the displacement and direction between two fixations. Other elementary features, for example, blinks, smooth pursuit motion and the angel of eye rotation within the head can also be determined from the raw eye tracker data stream.

The elementary features can then be interpreted to determine eye movement patterns. Eye movement patterns can include, for example, revisits, significant fixations, vertical saccades, horizontal saccades, short saccade runs, etc. In one embodiment, an eye movement pattern is a collection of elementary features that satisfies a set of criteria associated with a predetermined eye movement pattern template. In one embodiment, elementary feature data is analyzed after each saccade to determine whether a predefined eye movement pattern exists.

In one embodiment, the eye movement patterns are defined as follows; however, other definitions can be used for the eye movement patterns and other eye movement patterns can be defined. A "revisit" is a current fixation being within 1.2 degrees of one of the five most recent fixations, excluding the fixation immediately prior to the current fixation. In one embodiment, a "significant fixation" is a fixation of significantly longer duration when compared to other fixations in the same category.

A "vertical saccade" is a saccade in which the vertical (y) displacement is more than twice the horizontal (x) displacement and the horizontal displacement is less than one degree. A "horizontal saccade" is a saccade in which the horizontal displacement is more than twice the vertical displacement and the vertical displacement is less than one degree. A "short saccade run" is a sequence of short saccades collectively spanning a distance of greater than five degrees.

Eye movement patterns can provide information regarding the mental state of a viewer. For example, if a viewer makes a small saccade from a fixation, the viewer is making a knowledgeable movement because they are moving into an area visible through peripheral vision. As another example, a short saccade run indicates that the viewer is looking for an object locally. A large saccade after a significant fixation followed by a small number of small saccades indicates knowledgeable movement to a remembered location. Multiple large saccades indicate global searching, which occurs when the viewer is searching a large area for a target.

Eye movement patterns are interpreted to determine eye behavior patterns. An eye behavior pattern is one or more eye movement patterns that satisfy predetermined criteria. Recognition of eye behavior patterns does not require a priori knowledge of the viewer's visual field. Thus, mental states of the viewer can be inferred without reference to the visual field. The EIE can be used in both arenas: if context is known and provided then the EIE can make use of that information, but if not then it can still infer and interpret a great deal. For instance, one can determine when a page is being read as well as the general dimensions of the thing being read by looking at the pattern and overall shape of the group of eye movements even without explicitly knowing what the object being read is or even knowing in advance that it exists.

The examples and definitions of eye behavior patterns that follow are intended to be representative rather than exhaustive. Additional and/or different eye behavior patterns can be supported. Also, different definitions can be applied to the individual eye behavior patterns. A "best fit line" is a sequence of at least two horizontal saccades to the left or right, which can be further refined by taking the beginning and ending point of each saccade in the set and performing a Least Mean Squared fit to the data. "Reading" is a best fit line to the right (for English and other languages that are read left to right) or a short horizontal saccade while the current state is reading.

"Reading a block" is a sequence of best fit lines to the right separated by large saccades to the left with an optional small correction step, where the best fit lines are regularly spaced in a downward sequence and (typically) have similar lengths. "Re-reading" is reading a previously read area. "Skimming" is a sequence of best fit lines to the right joined by large saccades with a downward component, where the best fit lines are not regularly spaced or of equal length.

"Thinking" can be defined by, for example, several long fixations separated by short saccades. "Spacing out" can be defined by, for example, several long fixations separated by short saccades continuing over a long period of time. "Searching" is a short saccade run, multiple large saccades, or many saccades since the last significant fixation or change in user state. The example behaviors listed above are a brief overview of interpretative results that can be identified by an eye interpretation engine. The uses of eye interpretation outputs are not intended to be limited to the specific behaviors listed. That is, as eye interpretation technology evolves and eye interpretation engines become more sophisticated, the information and interpretations provided can be used by eye-aware applications to provide improved functionality.

Example Architecture to Provide Eye-Aware Applications

The eyetracker described herein may be associated with, or included in, any type of device for which eyetracking data may be useful. For example, in addition to computer systems with monitors or other display devices, the eyetracker may be in an automobile, a kiosk, a personal digital assistant (PDA), a toy, a game device, a billboard, a telephone, a cellular phone, a television or other monitor not coupled with a computer system, a refrigerator or other appliance, a set-top box, training equipment or educational device, such as books, or other devices providing visual information, glasses, a video conferencing system, mounted on a wall or in any space, etc.

Figure 2:
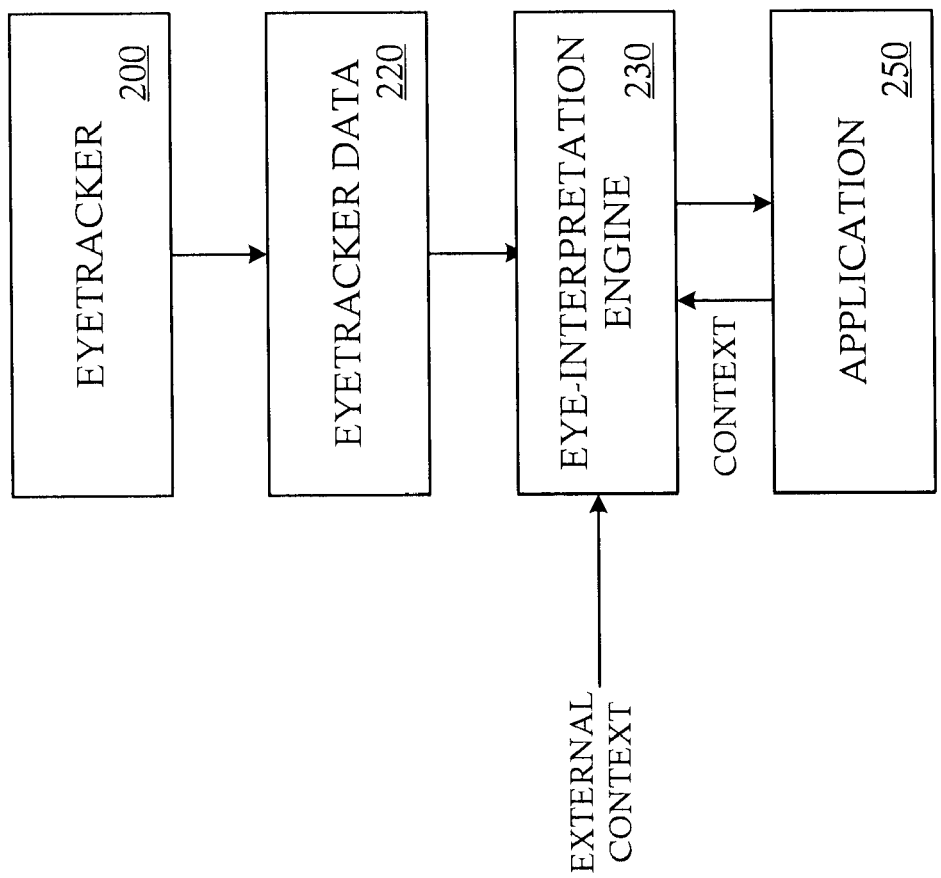
FIG. 2 is a conceptual illustration of one embodiment of an eye interpretation engine that interacts with an eye aware application.

FIG. 2 is a conceptual illustration of one embodiment of an eye interpretation engine that interacts with an eye aware application. In the example of FIG. 2, eyetracker 200 monitors one or more users of a device to provide eyetracker data 220 to eye interpretation engine (EIE) 230. In one embodiment, EIE 230 provides eyetracker data and/or multi-level (or higher-level) eyetracker data interpretations to application 250.

In one embodiment, application 250 may provide context data to EIE 230. Context data may include, for example, information related to what is displayed by application 250, visual state, application state, operating system state, environmental state and/or conditions, human state (e.g., biometric data), or other information related to a user interaction (current or past) with application 250. EIE 230 may also receive context information from a source external to application 250, for example a Web server or other source of information for a user of application 250 and/or eyetracker 200 or from another device directly or indirectly connected to the system (not included in FIG. 2).

The interaction of the components of FIG. 2 may be used to provide one embodiment of an eye-aware application that provides a better user experience than a non-eye-aware application. For example, as described in greater detail below, by providing intelligence to an application, the application can provide a customized experience to a user based on eyetracking data gathered from the user.

Figure 3:
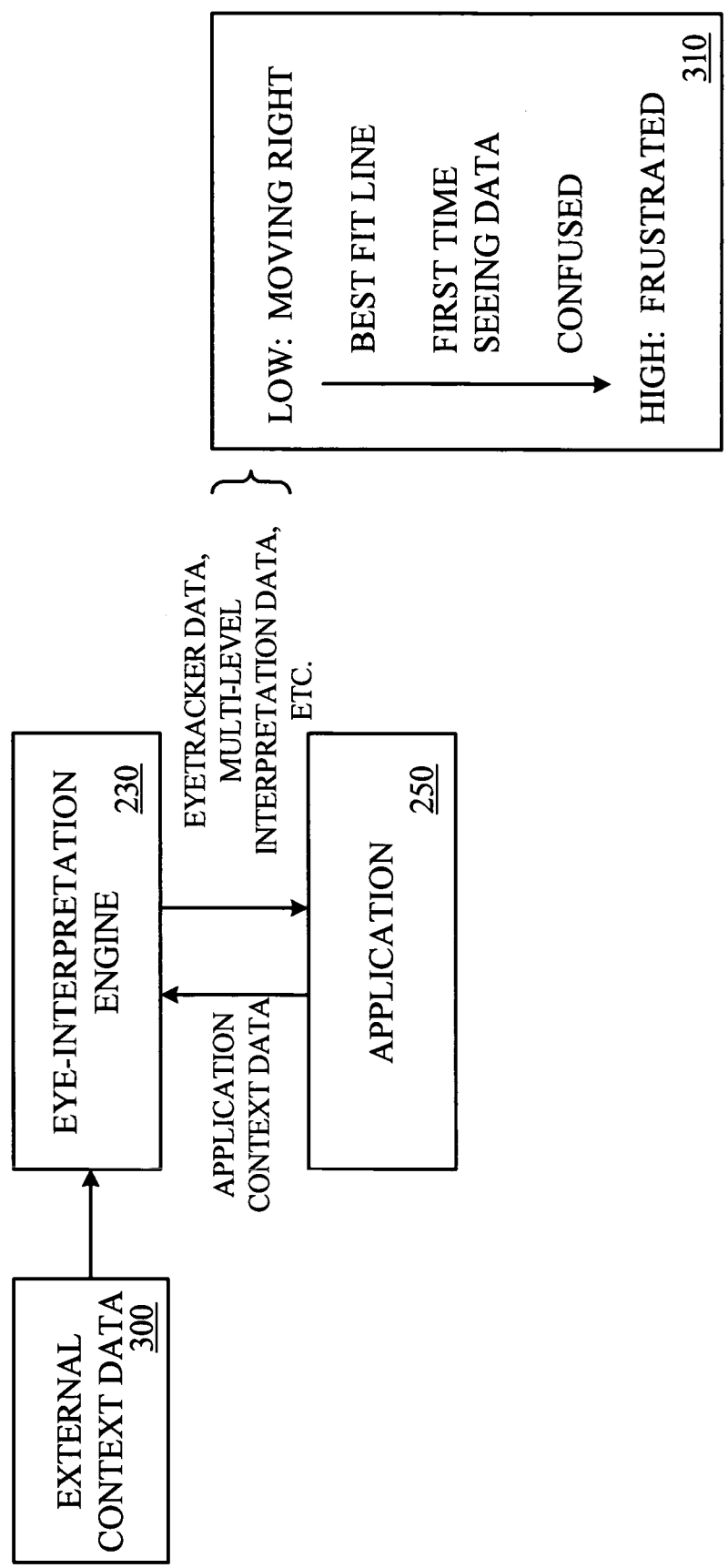
FIG. 3 is a conceptual illustration of one embodiment of an interaction between an eye interpretation engine and an eye-aware application.

FIG. 3 is a conceptual illustration of one embodiment of an interaction between an eye interpretation engine and an eye-aware application. In one embodiment, eye interpretation engine 230 may receive external context data 300 from one or more external sources. External context data 300 may include, for example, system and/or environment information, location and/or z-order of windows and/or objects, Document Object Model (DOM) of a Web page or application being viewed, current application process state and/or visual state, normalized galvanic skin measurements, other biometrics, other conceptual models and/or process models (task models, cognitive models describing the mental or physical steps or states required, etc.). External context data 300 can be used to supplement context data received by eye interpretation engine 230 from application 250. Context information received by eye interpretation engine 230 from application 250 can include one or more of the types of information listed above.

In one embodiment, eye interpretation engine 230 may provide to application 250 eyetracker data and/or multi-level interpretation information 310. Multi-level interpretation information 310 may include any type of information and/or analysis based on the eyetracking data. The example of FIG. 3 provides a listing of multi-level interpretations all of which may be simultaneously applied. Other interpretations and/or sets of multi-level interpretations can also be used including interpretations based on what is being actively focused on as well as what is being seen peripherally or not at all.

In addition to determining what a person has viewed and to what extent material has been viewed, the eye interpretation engine can also determine material that has not been viewed. An eye-aware application can react to what a user has not viewed as well as, or instead of, to what the user has viewed. Thus, while the examples that follow typically describe actions based on what a user has viewed, the techniques and concepts are equally applicable to reacting or responding to material that the user has not viewed.

Example Architectures for Supporting Eye Interpretation Functionality

Discussed above is the general interaction and high-level architecture of a system or network for supporting eye interpretation functionality. The examples that follow provide various configurations for supporting eye interpretation functionality. Other configurations not listed herein can also be used.

Figure 4:
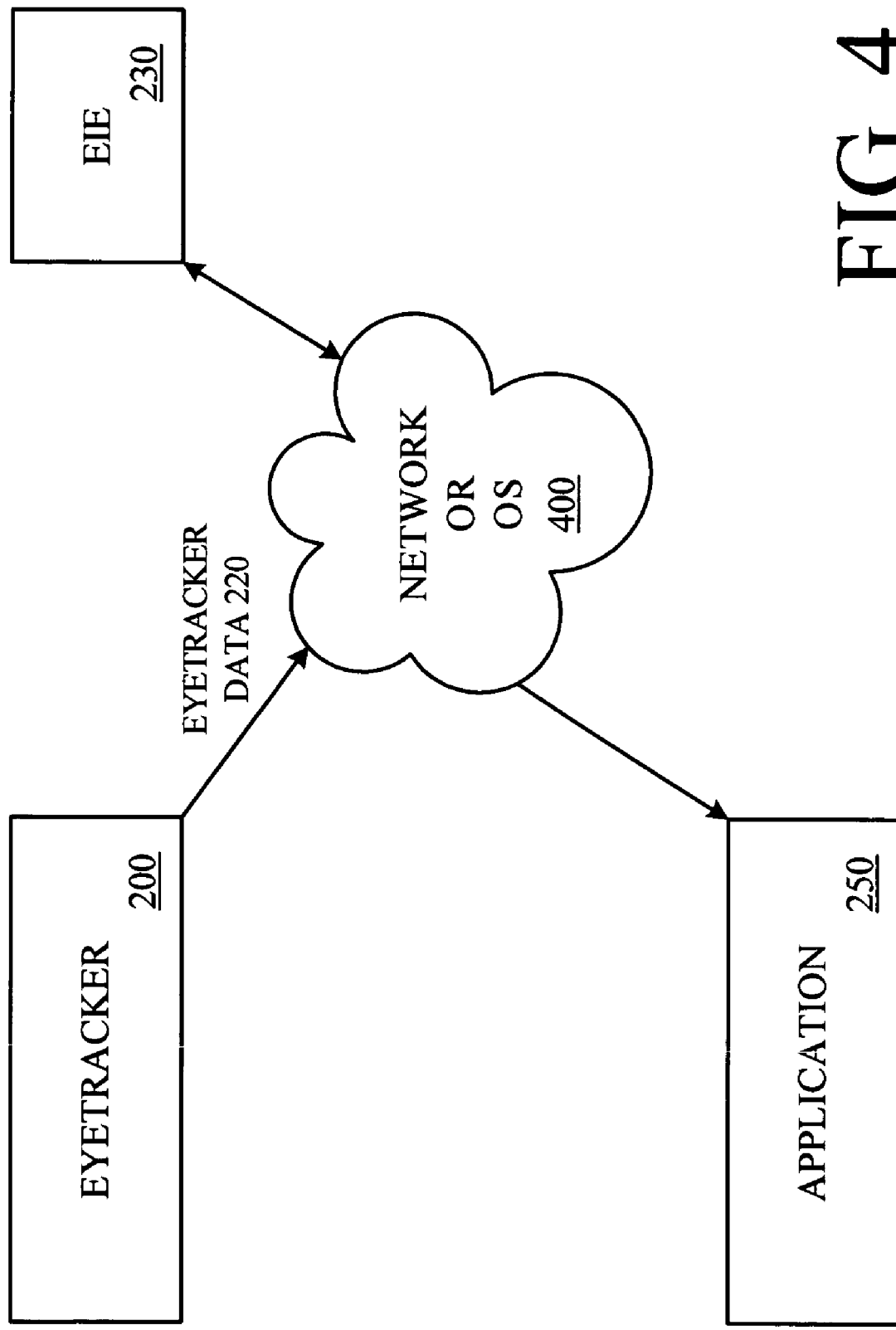
FIG. 4 is a block diagram of a first embodiment of a distributed architecture for supporting eye interpretation functionality.

FIG. 4 is a block diagram of a first embodiment of a distributed architecture for supporting eye interpretation functionality. In one embodiment, eyetracker 200 may be coupled with eye interpretation engine 230 by network 400, which can be any type of network (e.g., a wide area network, a local area network, a personal area network). Eye interpretation engine 230 may communicate with application 250 also using network 400. This allows eyetracker 200, eye interpretation engine 230 and application 250 to be located in one or more physical locations and may be supported by one or more electronic or optical systems. In an alternate embodiment, the communication functionality provided by network 400 can be provided by one or more operating systems running on one or more corresponding electronic systems.

Figure 5:
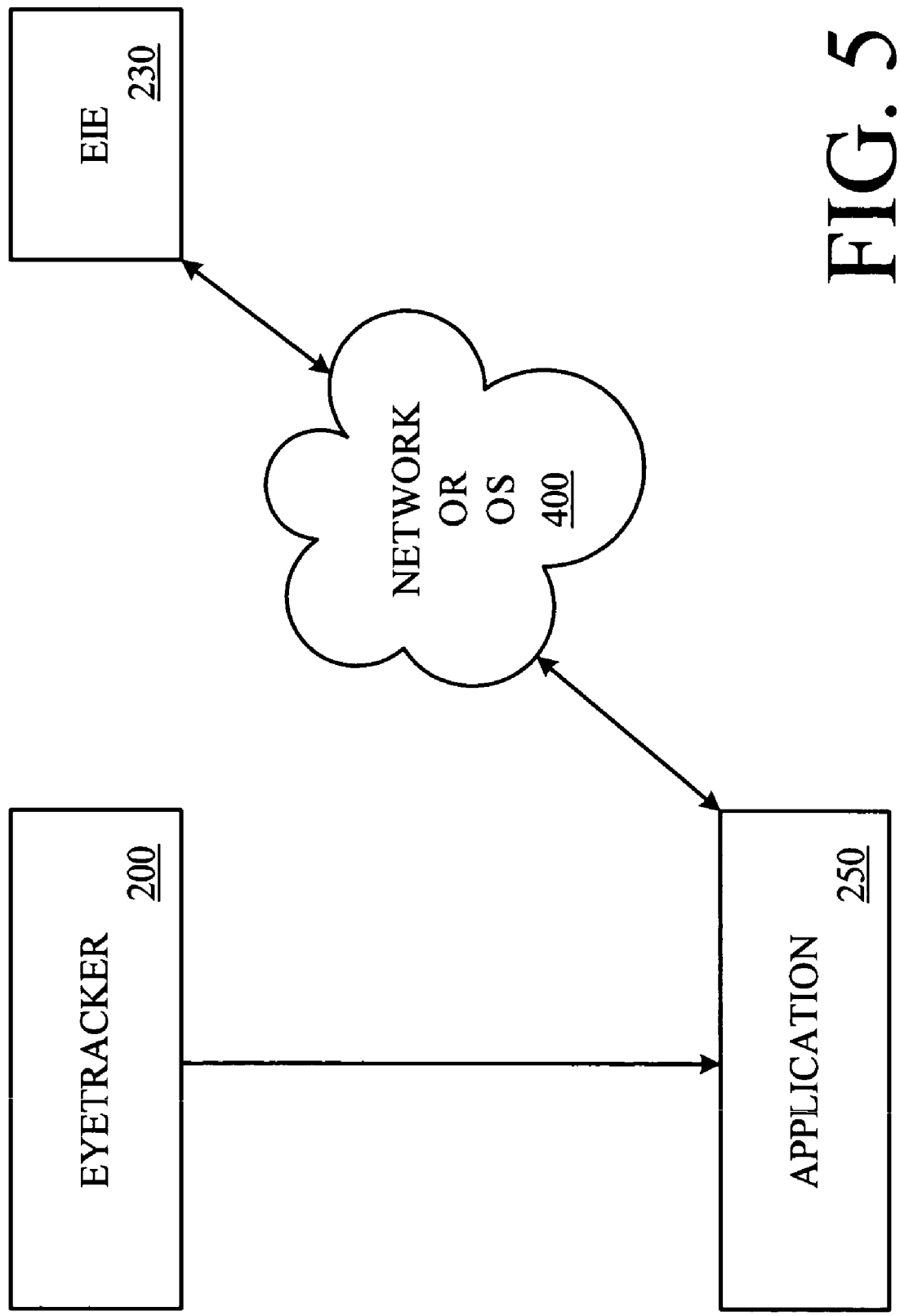
FIG. 5 is a block diagram of a second embodiment of a distributed architecture for supporting eye interpretation functionality.

FIG. 5 is a block diagram of a second embodiment of a distributed architecture for supporting eye interpretation functionality. In one embodiment, eyetracker 200 may be coupled with application 250. Application 250 may communicate eyetracking data or other information to an eye interpretation engine 230 using network 400. In an alternate embodiment, the communication functionality provided by network 400 can be provided by one or more operating systems running on one or more corresponding electronic systems.

Figure 6:
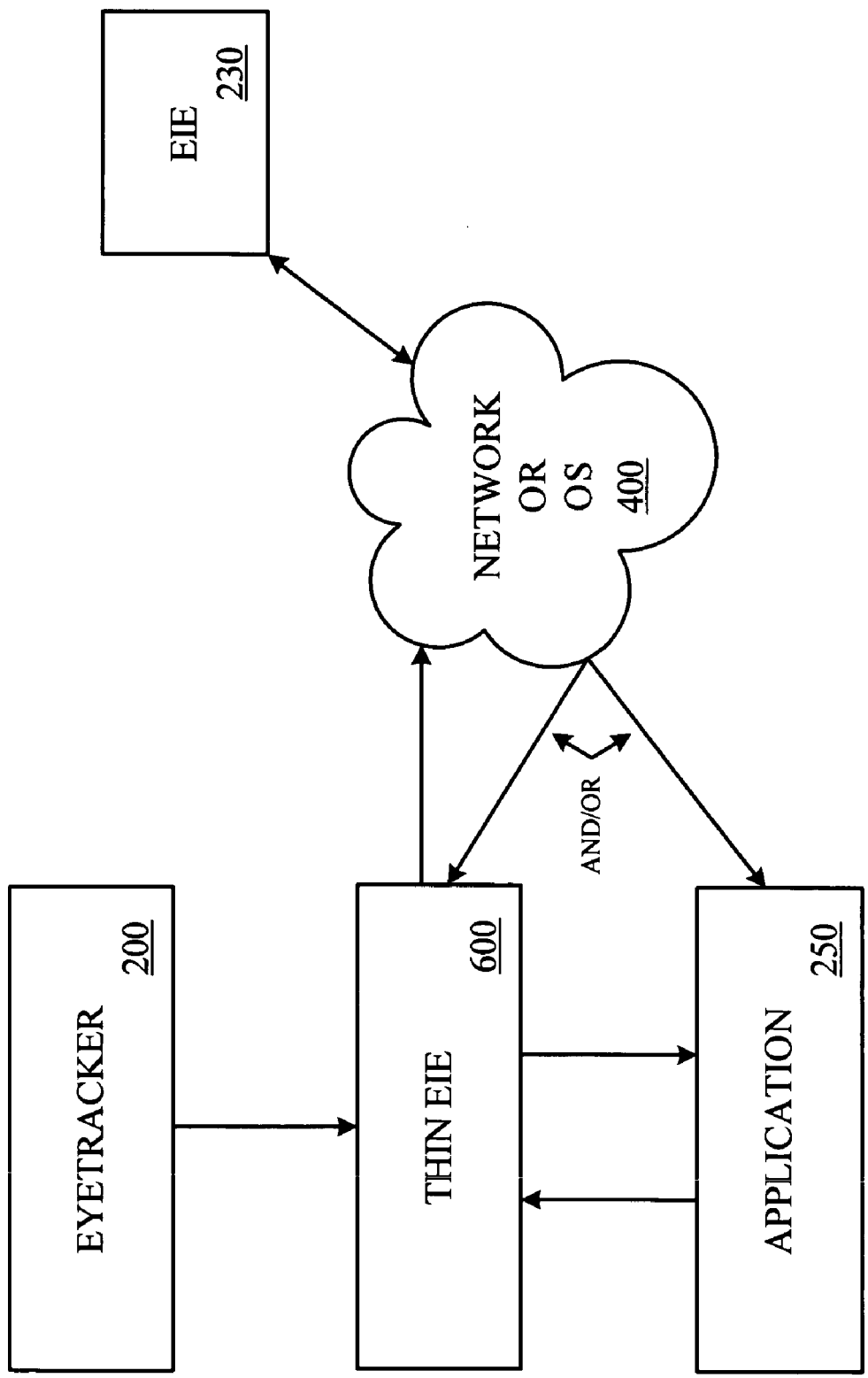
FIG. 6 is a block diagram of an embodiment of a distributed architecture for supporting eye interpretation functionality having a thin eye interpretation engine.

FIG. 6 is a block diagram of an embodiment of a distributed architecture for supporting eye interpretation functionality having a thin eye interpretation engine. In one embodiment, eyetracker 200 may be coupled with thin eye interpretation engine 600 and/or eye interpretation engine 230 (via network 400 or operating system), to communicate eyetracking data for higher-level analysis.

Thin EIE 600 may provide a reduced functionality as compared to EIE 230 in order to, for example, reduce bandwidth requirements associated with remote higher-level analysis. EIE 230 may communicate with thin EIE 600 and or application 250 via network 400 to provide a more through analysis of eyetracking data than can be provided by thin EIE 600. Application 250 can provide context information to thin EIE 600 and or EIE 230. Also, thin EIE 600 and/or EIE 230 may receive external context information (not illustrated in FIG. 6).

Figure 7:
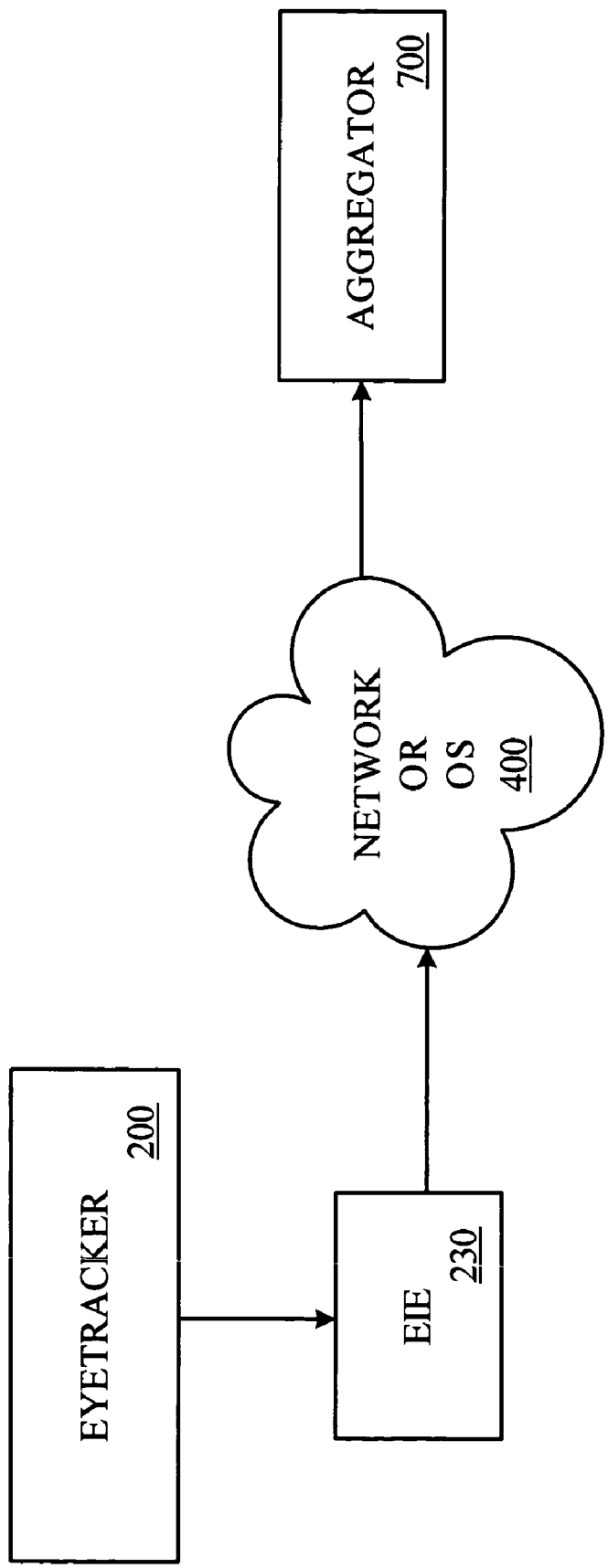
FIG. 7 is a block diagram of a first embodiment of a distributed architecture for supporting eye interpretation functionality having an aggregator.

FIG. 7 is a block diagram of a first embodiment of a distributed architecture for supporting eye interpretation functionality having an aggregator. In one embodiment, eyetracker 200 can provide eyetracking data to EIE 230, which can communicate the eyetracking data and/or higher-level analysis to aggregator 700 via network 400 (or operating system). In an alternate embodiment, eyetracker 200 may send eyetracking data to aggregator 700, which may provide eye interpretation functionality. Thus, aggregator 700 may generate group-level analysis, statistics and/or interpretations directly or by aggregating data from one or more eye interpretation engines. Aggregated information may be provided to EIE 230 or to one or more applications (not shown in FIG. 7).

Figure 8:
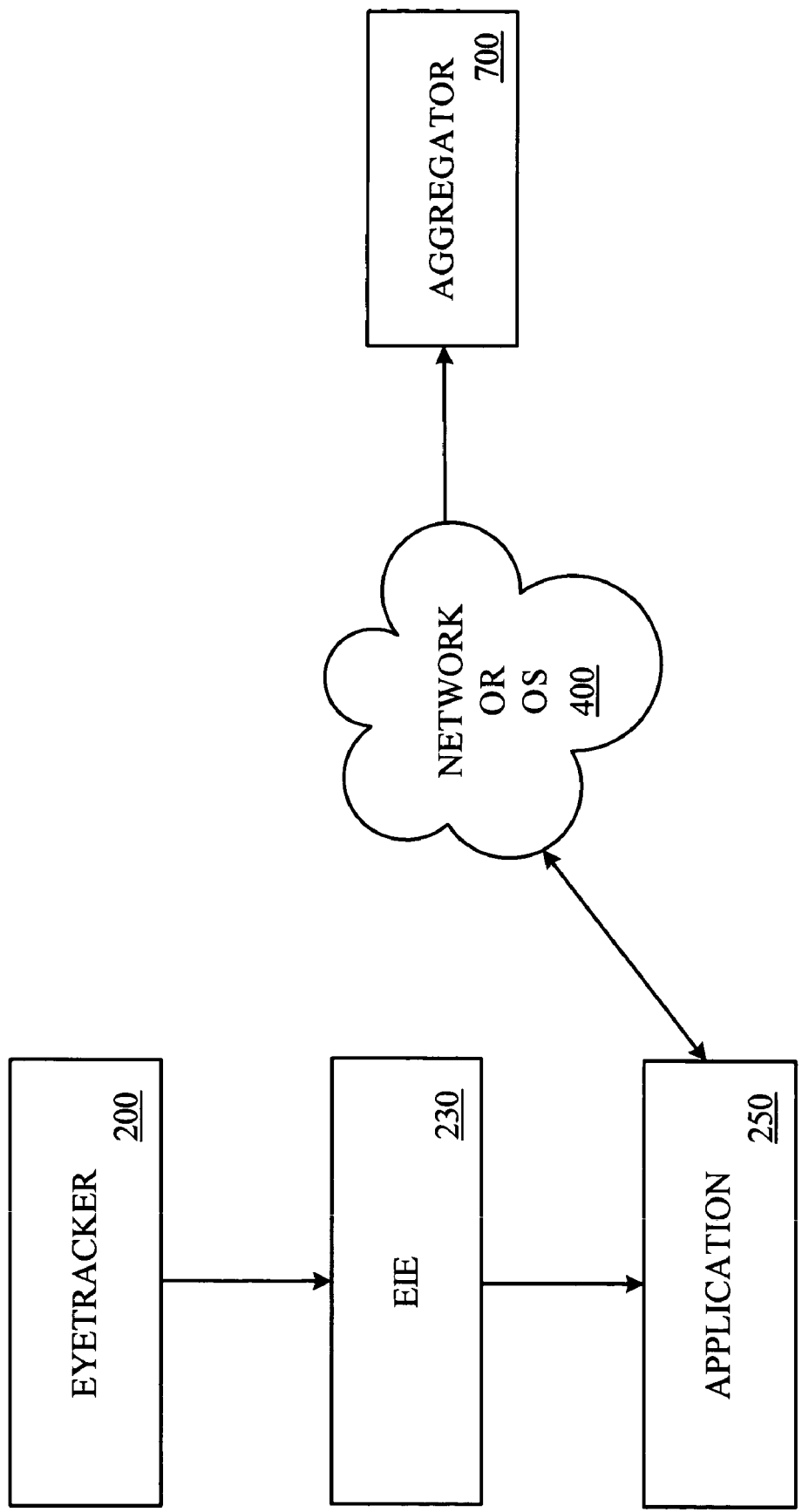
FIG. 8 is a block diagram of a second embodiment of a distributed architecture for supporting eye interpretation functionality having an aggregator.

FIG. 8 is a block diagram of a second embodiment of a distributed architecture for supporting eye interpretation functionality having an aggregator. In one embodiment, eyetracker 200 can provide eyetracking data to EIE 230, which can communicate the eyetracking data and/or higher-level analysis to application 230. Application 250 may communicate eyetracking data and/or higher-level analysis to aggregator 700 via network 400 (or operating system). Thus, aggregator 700 may generate group-level analysis, statistics and/or interpretations directly or by aggregating data from one or more eye interpretation engines.

Figure 9:
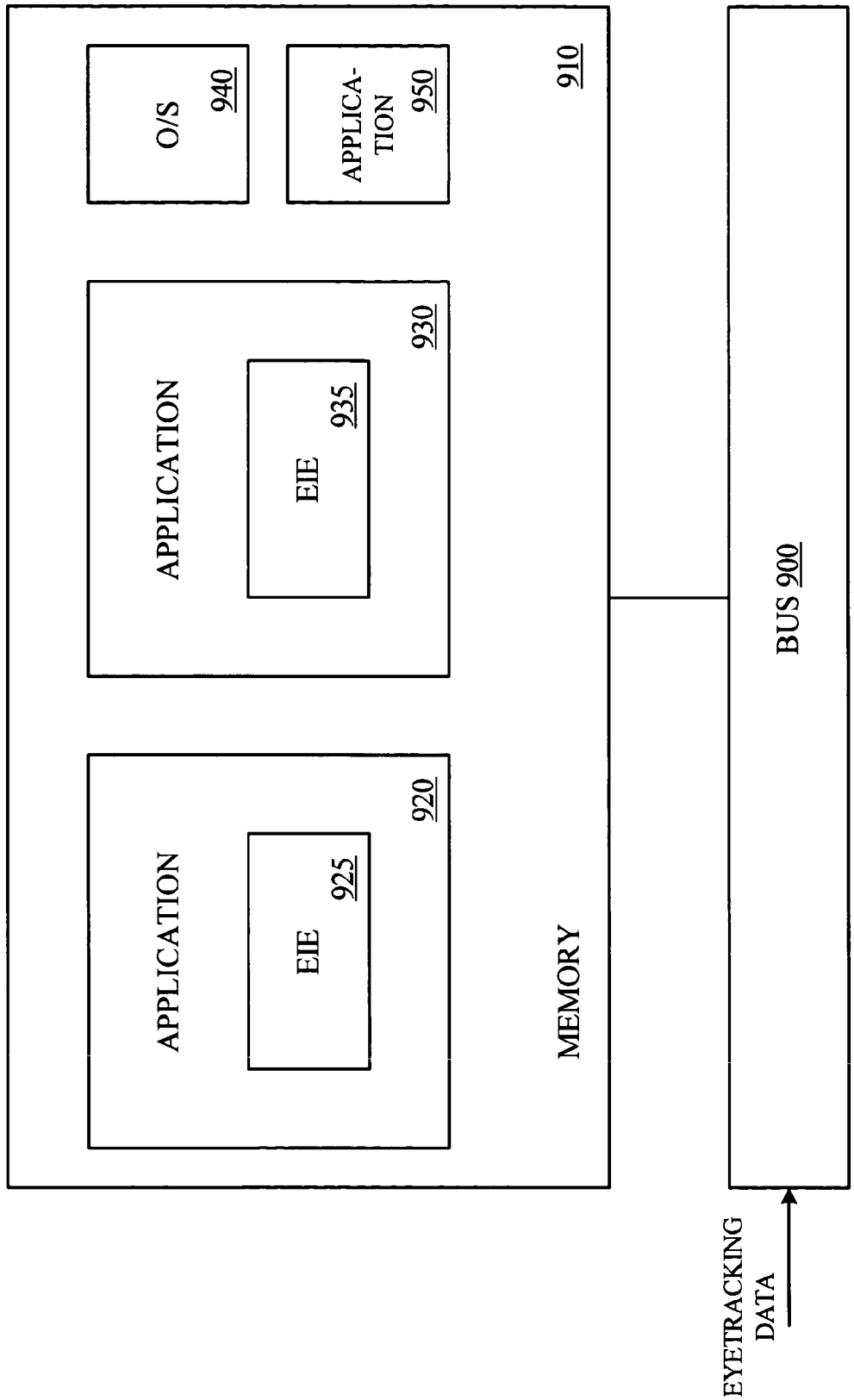
FIG. 9 is a block diagram of one embodiment of an electronic system running multiple applications having eye interpretation engines.

FIG. 9 is a block diagram of one embodiment of an electronic system running multiple applications having eye interpretation engines. Eyetracking data may be communicated to one or more applications stored in memory 910 by bus 900. Memory 910 may store multiple applications to be executed (e.g., 920, 930, 950) as well as operating system 940. Applications 920 and 930 may include eye interpretation engines 925 and 935, respectively, that may provide eyetracking data and/or higher-level analysis to the respective applications.

Figure 10:
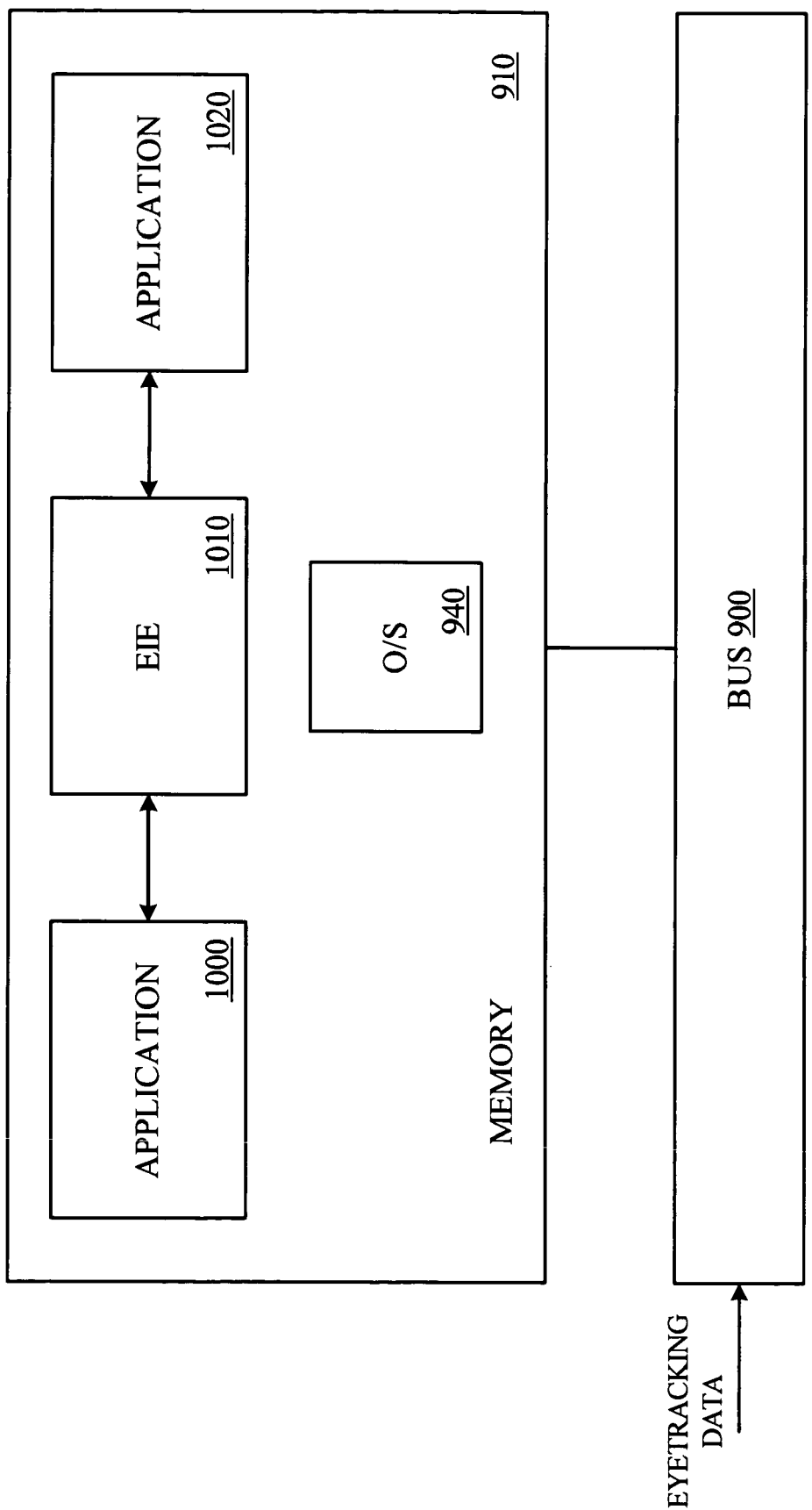
FIG. 10 is a block diagram of one embodiment of an electronic system running multiple applications sharing a single eye interpretation engines.

FIG. 10 is a block diagram of one embodiment of an electronic system running multiple applications sharing a single eye interpretation engines. Eyetracking data may be communicated to one or more applications stored in memory 910 by bus 900. Memory 910 may store multiple applications to be executed (e.g., 1000, 1020) as well as operating system 940. Applications 1000 and 1020 may communicate with eye interpretation engine 1010 that is also stored in memory 910 for execution. Eye interpretation engine 1010 may provide eyetracking data and/or higher-level analysis to applications 1000 and 1020.

Figure 11:
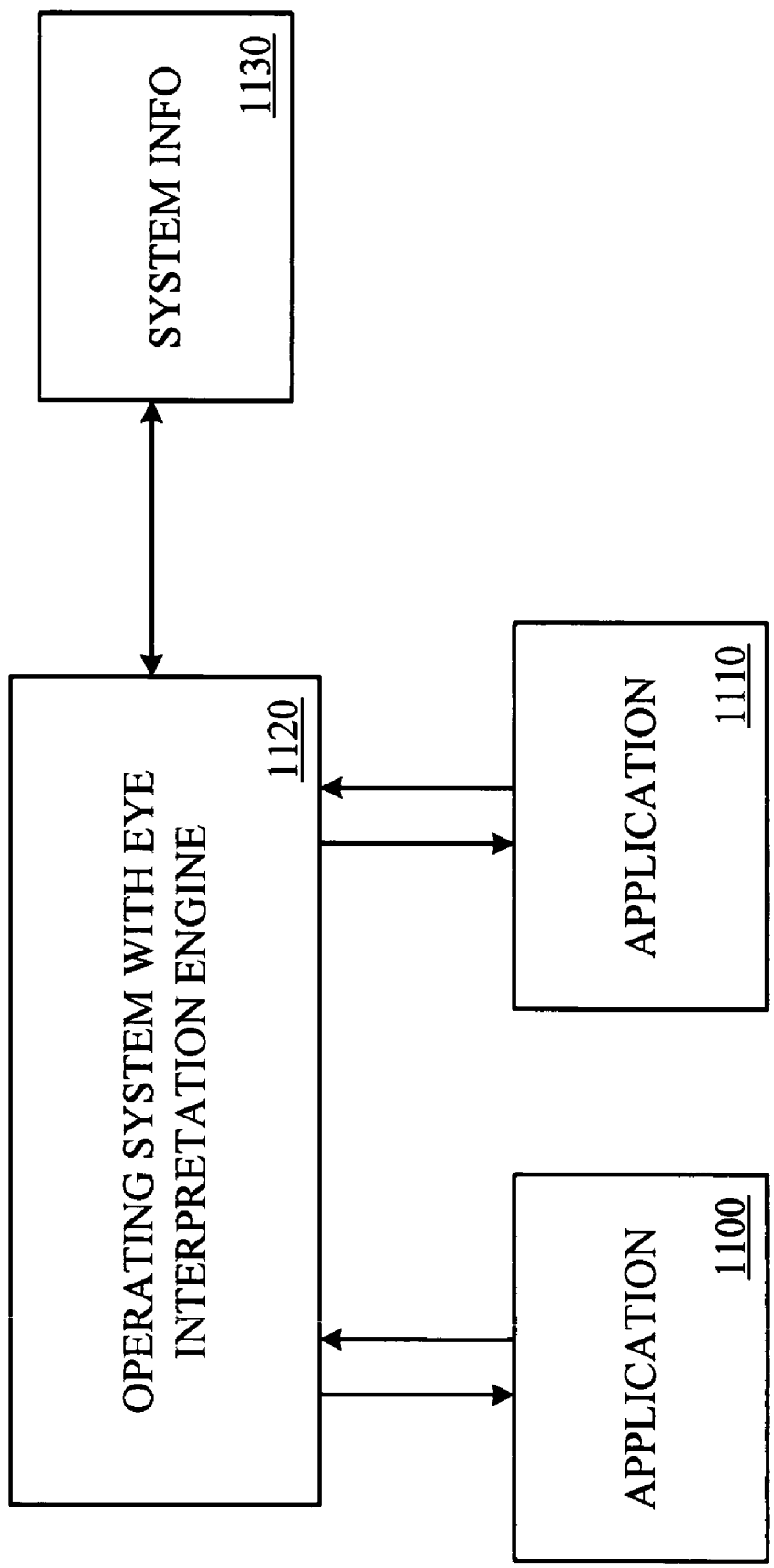
FIG. 11 is a block diagram of one embodiment of an interaction of multiple applications with an operating system having an eye interpretation engine.

FIG. 11 is a block diagram of one embodiment of an interaction of multiple applications with an operating system having an eye interpretation engine. In one embodiment, and operating system may include an integrated eye interpretation engine to provide operating system with eye interpretation engine 1120. In an alternate embodiment, an operating system may incorporate an eye interpretation engine as a plug-in or other module. Applications 1100 and 1110 can interact with operating system with eye interpretation engine 1120 for both system functionality as well as eye interpretation functionality. Operating system 1120 may have access to system information 1130 that may provide context information that can be used with eyetracking data to provide eye interpretation functionality.

Example Applications Using Eye Interpretation Functionality

In the examples that follow several applications of eye interpretation functionality are provided. These examples are not intended to provide an exhaustive listing, but to provide an overview of the ways in which an application can use data and/or interpretations from an EIE.

In one embodiment, content provided to a user being monitored by an eyetracker can be filtered based on current behavior as determined by the eye interpretation engine. For example, if the eye interpretation engine determines confusion and/or heavy re-reading and/or slow reading, or other high-level interpretation indicating a heavy mental load, the content provided to the user can be modified to be less complex. As another example, content provided to the user by the application can be filtered or modified based on what the EIE reports has, or has not, been read or viewed by the user.

In one embodiment, portions of text and/or an interface may be categorized as one of the following: never made visible to the user, visible to the user but ignored by the user, glanced at by the user (e.g., 1 or 2 fixations), looked at by the user (e.g., small number of fixations relative to surrounding area), skimmed by the user (e.g., intermittent reading separated by repositioning saccades and glancing), and read. In alternate embodiments, other and/or different categories can also be used.

In response to the categorization of a passage of text or a portion of an interface, important text not sufficiently reviewed by the user can be re-presented in a stronger, more attention-grabbing format. A "related topics" list or text can be dynamically built based on the response of the user. Users can also be categorized (e.g., as new or as returning users) based on how content is initially viewed by the user. Categorization of the user can be used to filter and/or dynamically modify content that is provided to the user.

Figure 12:
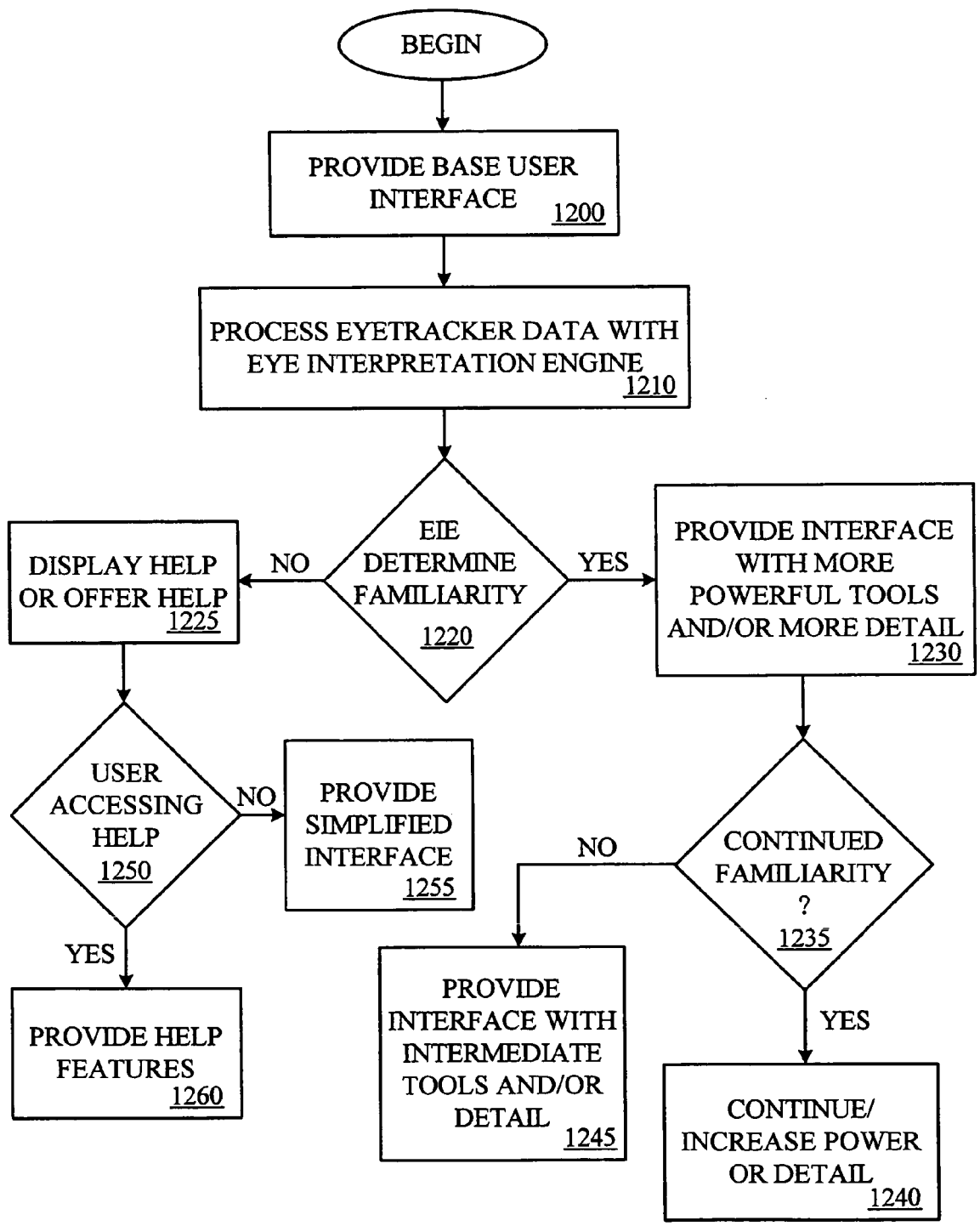
FIG. 12 is a flow diagram of one embodiment of a technique for changing the display of a user interface based on familiarity and/or expertise rating as determined by an eye interpretation engine.

FIG. 12 is a flow diagram of one embodiment of a technique for changing the display of a user interface based on familiarity and/or expertise rating as determined by an eye interpretation engine. The example of FIG. 12 provides one strategy for providing a dynamically adaptable user interface. Many other variations on the strategy of FIG. 12 can also be provided using an eye interpretation engine.

A user may be provided with a base interface, 1200. The base interface may include, for example, a set of features that a typical user may expect to use. Eyetracking data corresponding to the user are processed with the eye interpretation engine, 1210. The eye interpretation may determine whether the user is familiar with the interface provided, 1220. The eye interpretation engine may also provide additional information based on eyetracking data.

If the eye interpretation engine reports that the user is not familiar with the interface, 1220, a help screen or an offer to provide help may be displayed, 1225. If the eye interpretation engine determines that the user is accessing the offered help, 1250, additional help features may be provided 1260. If the eye interpretation engine determines that the user is ignoring the help, 1250, a simplified interface may be provided, 1255.

If the eye interpretation engine determines that the user is familiar with the interface, 1220, an interface with more powerful features and/or more detail may be provided, 1230. If the eye interpretation engine determines a continued familiarity with the modified interface, 1235, the modified interface may be maintained or the interface may be further modified to provide still more powerful features and/or detail, 1240. If the eye interpretation engine determines a confusion or lack of familiarity with the modified interface, 1235, an intermediate (or the base) interface may be provided, 1245.

An application could also enable text content optimization by using data returned from an EIE to indicate those areas where groups of people tend to skip, skim, or reread areas of content. This would be enabled by the application receiving from the EIE those areas which are skipped, skimmed, or reread across a group of people.

Presentation of data in "slide" format can be controlled using eyetracking data. For example, an auto-paced slide show that makes use of the output from an EIE in real-time could stay on the current slide (not move on) while the EIE reports that the individual or more than 40% (or any other threshold value) of the group viewing the presentation is still reading the text on the slide.

For reasons of simplicity and clarity the following examples will focus on Web pages. However, while the examples provided are in terms of Web pages, the technique and concepts are not limited to Web pages and are equally applicable to a broad range of applications and classes of interactions.

In one embodiment, one or more people could use Application A, while being observed by Application B, which receives an interpretation of the eyetracking data from an EIE, that then modifies Application A based, at least in part, on the interpretation of the eyetracking data received by Application B. One or more people using a Web page in a Web Browser could be observed by some recording software that directly or indirectly via the web interacts with an EIE in real-time or at a later time in order to provide interpretations of the eyetracking data collected while the one or more people used the Web Page in the Web Browser.

The output from the recorder's use of the EIE could then be used to modify the content or layout of the Web Page similarly to other examples in this patent, but specifically one embodiment would be to move a piece of content further up the page or further down the page contingent on the percentage of people that saw the content. The preferred embodiment of this particular application would be to reorder an element in a list based on the percentage of people who had that element visible on the screen that viewed it, as long as the number or percent of people seeing it is greater than a chosen threshold of the number of people that saw the page at all. For example, if the threshold required to judge an element worthy of moving is if 7 people see it, then if 50 people saw a web page, and element 3 on the page was visible to all 50 people but viewed by 20 people (40% of the people who had it visible on the screen), but element 8 was only scrolled into visibility by 30 people but 20 of those 30 people saw element 8 (67% of the people who had it visible on the screen, and above the threshold of 7 people as a minimum), then element 8 would be moved up the page above element 3.

In another embodiment, one or more people could use Application A, while being observed by Application B, which receives an interpretation of the eyetracking data from an EIE, that then modifies or creates or activates Application C based, at least in part, on the interpretation of the eyetracking data received by Application B. One or more representative demographic groups could have data collected on their viewing of a Web page A, recorded by Application B, similar to the description above, that then uses the results from the EIE to modify or create a new layout for wider distribution on the Web (though people from the initial group tested may or may not ever see that page).

One embodiment of this may be to test a small group of people on prototype Web pages with an EIE providing results that are then used, at least in part, to configure or modify or create or select a Web page that is released onto the Web for the general public.

In another embodiment, one or more people could use Application A which accesses an EIE and uses the results, at least in part, to modify, invoke, or remove content from itself. The preferred embodiment of this is an Web browser that has an EIE embedded in itself, or is accessible via the Operating System or via the Web collects eyetracking data on people as they use Web pages, which the EIE then interprets. The EIE then reports back to A (or, clearly, it could report to any other application as well) which ads are not seen, or are seen only in peripheral vision, or are only seen after a mouse click and based on that interpretation can choose or randomly present a different set of advertisements—this application could do this one time or iteratively in an attempt to improve the experience on the Web page. The EIE while providing interpretation about what is directly seen can also provide interpretation and recommendations based on what is not seen or what is seen only in peripheral vision by one or more people.

Figure 13:
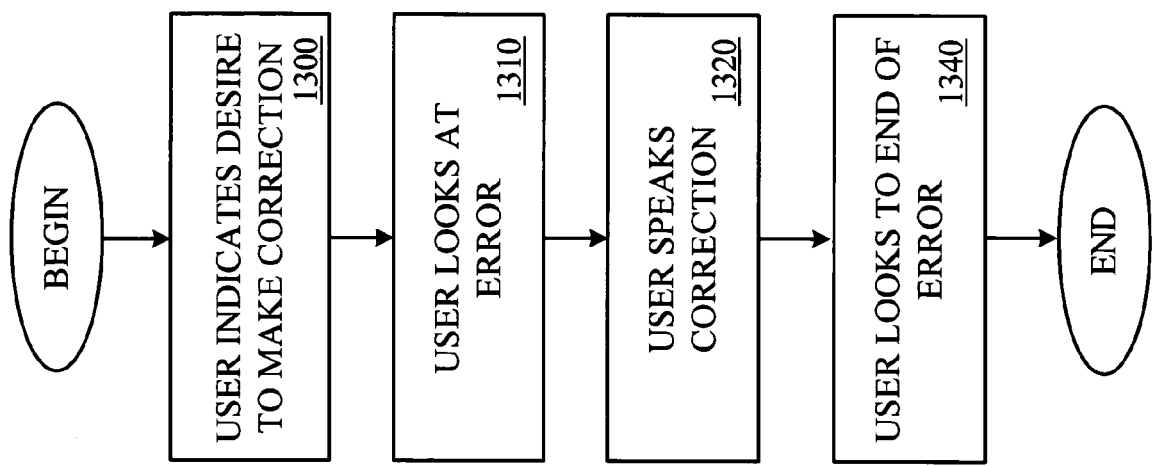
FIG. 13 is a flow diagram of one embodiment of a technique for correcting speech recognition mistakes using an eye interpretation engine.

FIG. 13 is a flow diagram of one embodiment of a technique for correcting speech recognition mistakes using an eye interpretation engine. Eyetracking can be used, for example, to correct errors in text generated by speech recognition. The example of FIG. 13 describes one technique for making corrections using eyetracking; however, other techniques for making corrections using eyetracking could also be supported.

In one embodiment, a user may place the speech recognition tool in correction mode by indicating a desire to make a correction, 1300. The switch to correction mode can be accomplished, for example, by clicking on a button, speaking a pre-selected phrase (e.g., "that is wrong" or "correct that"), and/or looking to a pre-selected location, etc.

In one embodiment, the user looks to the error, 1310. For example, the user may look to the beginning of the erroneous text. The user may then speak the correct text, 1320. The user may look to the end of the erroneous text, 1340 to delimit the end of the section of text to be corrected. The text generated by the user's spoken words can be used to replace the erroneous text.

In another embodiment, as a user reads an incorrect piece of text the applications allows the user to indicate that an error exists, for instance by saying "that's wrong." The end-point of the reading is then marked by the application. The user then looks at the beginning of the error (thereby marking the beginning of the area to be replaced) and speaks the correct text—this process could be further refined by doing matching on the edges to adjust a word either way to align the new utterance with the old text. Voice annotation of content can be implemented using a method similar to the error correction method, whereby the user can read the text and do the same steps as for an error but say "annotation" instead of "that's wrong."

An EIE can be used for applications where visual search is important (for instance, in scanning radiological images for cancerous growths). Such an application could make use of an EIE to display as-requested or periodically those areas of the image or device which have already been examined, glanced at, or ignored.

Eyetracking can also be used in instructional situations, for example, reading instruction. Eyetracking data combined with context information can indicate a passage or material that may appear difficult for a reader to comprehend. Other types of instructional applications can also be supported.

As another example, program or device using speech generation and an EIE may prompt a student who is learning to read in multiple ways, such as "Mary, it's great that you examined these areas of the page" while highlighting the ones that are good to examine which she examined or could highlight areas that are important to look at, such as call-out boxes, which were ignored or only glanced at and say, "These areas (call-out boxes) are important to look at (or to look at first before the rest of the page)," or could say "it's good that you read every single word on this page, but it is better to first skim the page looking at the headings and call-out boxes and then go back and read everything."

The program or device could provide this functionality by querying the EIE at a logic "teaching opportunity" (for instance, before the student moves on to the next page or area) to find out which areas of a page where examined, glanced at, read completely, or skimmed (either ordered by time or not). If an object on the page received more attention as reported by the EIE than is appropriate (based on the program or device's rules which would be determined by research and expertise in education and not related to the EIE per se) then the program could coach the student as designed by the educational subject-matter experts who designed the program.

Eyetracking can also be used, for example, for tool and/or palette selection or manipulation in a graphical environment. In many graphical environments a color palette and/or one or more tool palettes are provided for use in manipulating displayed data. In one embodiment, tools or options to modify what is displayed may be controlled by a user's eye movements as interpreted by the eye interpretation engine. For example, looking at a tool may not select the tool if the eye interpretation engine determines that the user is searching or looking around at the options and/or tools. However, if the eye interpretation engine determines that the user looks to a tool with purpose, the tool may be selected by the application.

Figure 14:
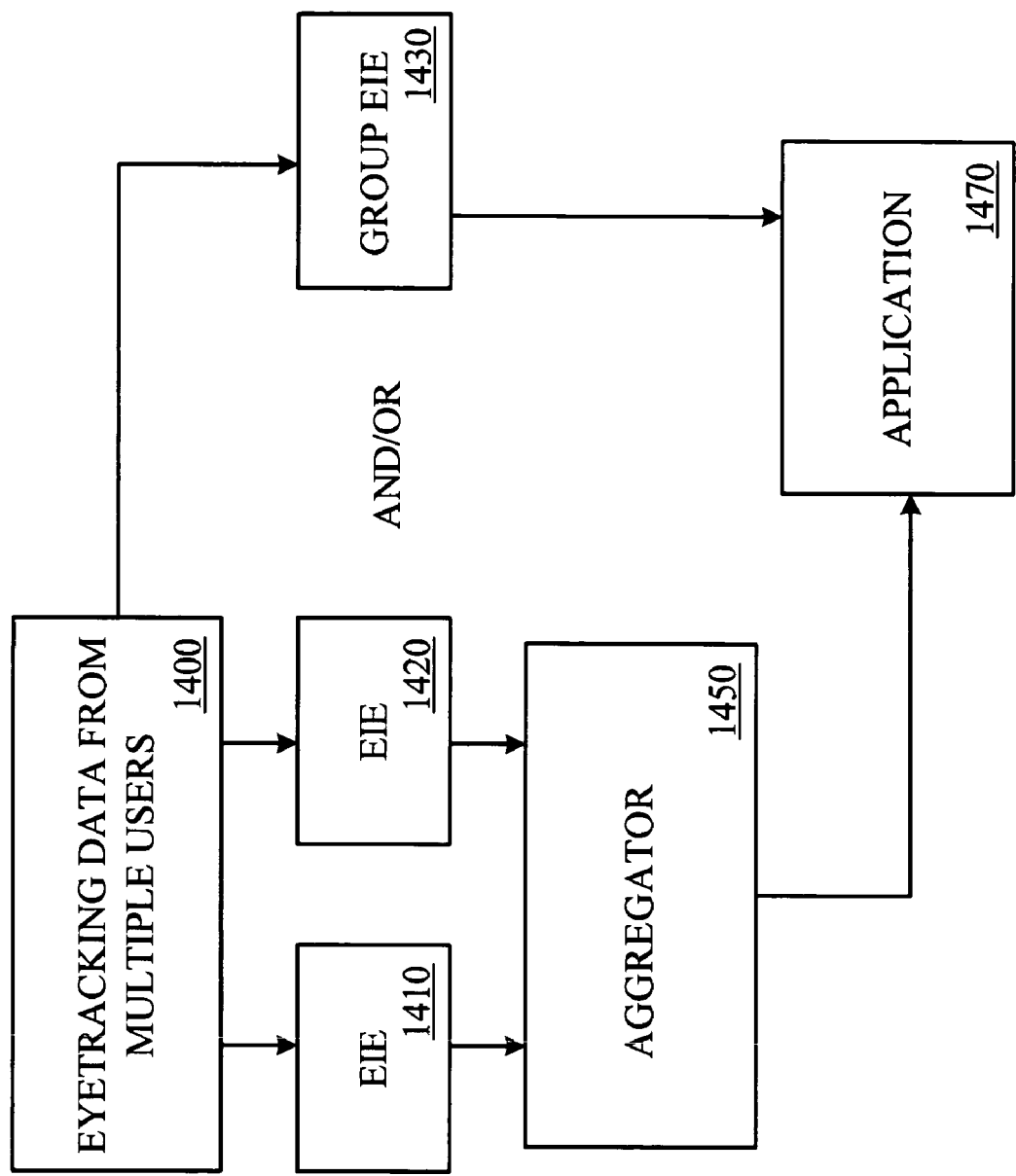
FIG. 14 is a block diagram of one embodiment of an architecture for providing dynamic content based on eye-tracking data from multiple users.

FIG. 14 is a block diagram of one embodiment of an architecture for providing dynamic content based on eyetracking data from multiple users. Eyetracking data from multiple users 1400 may be provided to multiple eye interpretation engines (e.g., 1410, 1420) and or to group eye interpretation engine 1430. In one embodiment, group eye interpretation engine 1430 performs higher-order analysis and interpretation on eyetracking data from multiple users.

Multiple individual eye interpretation engines (e.g., 1410, 1420) provide eyetracking data and/or higher-order analysis to aggregator 1450, which compiles data received from the eye interpretation engines. In one embodiment, aggregator 1450 may perform further analysis. Eyetracking data and/or higher-order analysis from aggregator 1450 and/or from group eye interpretation engine 1430 may be provided to application 1470 that may, for example, dynamically vary content based on the data received from the eye interpretation engines.

In one embodiment, application 1470 dynamically serves data, content, video and/or other data based on a determined group behavior. For example, a highest occurring behavior or an "average" behavior may be used to determine content to be provided. Thus, if, for example, application 1470 is a Web server, content can be provided based on a determined greatest interest of the group. As another example, a movie plot can be modified based on reactions from the audience viewing the movie.

As another example, application 1470 can modify an interface or layout based on group behavior or response to the interface or layout. One technique may include providing many visual components and determine which components draw the most interest from the users. The visual components that provide the desired result, as reported by the EIE in conjunction with the applications business rules, can be maintained or enhanced while the other components can be removed or minimized.

An alternative embodiment of this would be to start with a base layout, and then feed data into an EIE that came from telling a group of people to sequentially find elements on a list—the list being comprised of elements that are important to the business goals. Given that the people's eyetracking data may document each of the places visited in order, which documents the ordered locations they expected the object to be in, the EIE can then compute a Least Mean Squared optimization of the placements of the objects on the layout. This process can be iteratively done.

When aggregating group eyetracking data, a behavioral baseline, or reference for future comparison may be generated. The baseline can be used when interacting with an individual or a group. For example, data may be provided to an application as to the current user's reading speed and how that determined reading speed relates to a group baseline or to a group subset baseline. As another example, reading improvement or other diagnostics can be applied to a user to report progress and/or problems. Various baselines can be used, for example, a national or regional sample, a local peer group, etc. An application may generate a marked or annotated version of the content viewed by the users with indications corresponding to group reactions, for example, lack of comprehension, etc.

A Web site, application, or other content can be rated, ranked or sorted based on aggregated eyetracking data. Feedback can be provided that indicates a rating on various scales (e.g., confusion, amount read, time spent reading and/or glancing, ability to focus, amount of focus on various portions, etc.). The ratings or rankings can be used to make modifications or take relevant actions.

Aggregation of eyetracking data can also be used for test administration purposes. For example, for a structured test, a test plan can be administered through a Web page where users log in and an application may launch one or more pages for which eyetracking data is logged. The logged eyetracking data may be analyzed by, for example, a central eye interpretation engine. For an unstructured test, users of a Web page may be allowed to freely use the Web page or any Web pages while eyetracking data is logged. The logged eyetracking data may be analyzed by a central eye interpretation engine.

Applications for test administration include, for example, large, decentralized research studies that use multiple eyetrackers and many users to study a single item or element. Alternatively, less structured techniques for capturing viewing behavior that can be analyzed can also be provided. For the decentralized study scenario, data transferred from the individual eyetrackers to the central analysis tool may include eyetracking and/or stimulus data. For example, the elements that were viewed and the type of viewing those elements received may be communicated. More detailed analysis may also be provided.

Another aggregate eyetracking application may include an application, in conjunction with a set of rules determined by research which is updated as social norms change, could use an EIE in conjunction with a face and/or body tracker pointed at another person to provide feedback to the user as to whether she is looking for too long or too short (or at all or not at all) at another person's eyes, cheeks, lips, or other parts of the body or in a pattern which is appropriate/inappropriate. This could help, for example, autistic children learn the rules associated with normal social interaction, as well as business people who work in cross-cultural environments.

Another application for dynamic content may be, for example, an interactive "Where's Waldo" that taunts a user based on results from an EIE (interpreted eye-movement patterns). This can be used, for example, for an on-screen game or for a board game or device that has an embedded eyetracker.

In one embodiment, the EIE may hold a list of examined areas (ordered by time) as well as a list of areas glanced at and reports this directly or when queried by the game. The game then can "taunt" the player by determining that the player has already examined an area close to where the hidden element is hiding and could use speech output to say "You already looked near it! You were so close!" and could add "and now you are so far from it!" if the player is not currently looking near the hidden element as reported by the EIE.

A shooting-style arcade game could be more emotionally stimulating by reacting to where players have looked. For example, in an "easy level," the game could help the person feel that they have mastered the game by popping up opponents (that require quick reflexes to shoot down, for instance) in an area or near the area (within clear peripheral vision as reported by the EIE) where the person is intently focusing as reported by the EIE. In a "difficult level," for example for a game where there is a lot of camouflage where the player needs to search for the opponents that pop-out and shoot at the player, the game could heighten the emotional impact of the game by popping up opponents in an areas that the EIE reports has been recently glanced at but not examined which is still within peripheral vision as determined by the EIE, which could lead to the player feeling "OH, if only I had examined that area better!" particularly if the player's game character died—this could be much more appealing to the player than just blindly getting shot and killed from an area where they didn't even ever see the opponent (assuming that being fully blind-sided by a never seen opponent and suddenly dyeing in a game is less fun than seeing the opponent for a split second in which the player could react before the player's character gets blasted and dies). Adding the capability to the game would entail setting the coordinates of a pop-up opponent to be within one of the areas returned recently by the EIE as a "only glanced at" and "within current peripheral vision" area.

As another example, testing using an EIE to determine optimal "find the word" puzzle layouts for various levels of difficulty. Multiple templates of "find the word" puzzles could be tested using an EIE upon various demographic groups of various skill levels to determine which areas and directions various groups tend to focus on in order to improve layouts that are optimally easy (yet not trivial) or difficult for the spectrum of beginners to expert "find the word" puzzle players. Such an application could use the EIE to determine which areas within each template are focused on and which direction people's eyes tend to go throughout the experience (in order to know where and in which direction to hide words so that they are easily found initially or designed to be found later). The determination of the layouts could even be randomly generated or guided by an algorithm to present various permeations of layouts to people which the viewing patterns are then processed via an EIE to compare the results generated by the EIE for each layout.

An eyetracker and an EIE embedded in a hat or in some other piece of clothing or device on a baby/child could track the amount of time a parent (or someone or group of adults) looks at the child's eyes, face, and/or body (or near each of these areas) and could provide feedback to the parents as statistics reported by the EIE (such as number of times the adult looked at the baby, the amount of time, as well as patterns that would further break down the "amount of time spent looking" into further categories such as amount of "short duration" times as opposed to "long duration" interactions). Additionally, an eyetracker could be pointed at the baby/child's eyes so that the EIE could determine the amount of time that the baby was looking into the eyes of the adult as the adult looked into the eyes of the child and could report this to one or more applications. The dynamic tracking of where the child/adult are relative to each other and the eyetracker/EIE could be accomplished by using a suitable position-reporting device or set of devices.

By embedding an EIE and one or more eyetrackers into a device, the device could determine when no-one was looking and whether there was a typical amount of time which people did not look at it, and could then move or change itself during that time. This would make a party gag where a piece of sculpture or furniture could move or change when people wouldn't directly notice. Another way the EIE could be used in this would be for it to determine when no-one is directly looking at it but that enough (1 or more) people have the object in their peripheral vision so that when it moved it would be noticed but upon direct examination by one or more people the object would be still.

An application or device could use an EIE engine to determine which things in a room or environment have not been directly or indirectly viewed in a long time (weeks or months, for instance), and could suggest to a user things they could read or do (games) which the EIE reports have not been viewed for quite some time. Such an application could make use of speech recognition software or body and/or object tracking applications in order to know where objects and/or people are in an environment as well as to provide a way that people could easy note that an object is of interest to them currently, or in the past when they acquired the object or are about to put it onto the shelf (e.g. "this is a good book!") as well as whether it has been overlooked for a user-specified amount of time. An alternative application similar to this could use an EIE over time to suggest reading material that hasn't been read in a long time or at all.

For blind people, an "alternative EIE" that does not track eye-movement and can emulate the output from a standard EIE in order to interface with eye-aware applications. This could be used by blind people so that they can interface with software that is eye-aware by using an alternative device (an "alternative EIE") that puts out the same high-level analysis of behaviors that an EIE creates but which uses different patterns of inputs in order to determine which high-level analysis of behavior to report. This could also be used in testing of eye-aware applications automatically (an eye-aware application can publish the behaviors it reacts to so that EIE engines or other "alternative EIEs" can interact with it) as well as to open up enabling other patterns to be used in a fashion similar to an EIE.

Figure 15:
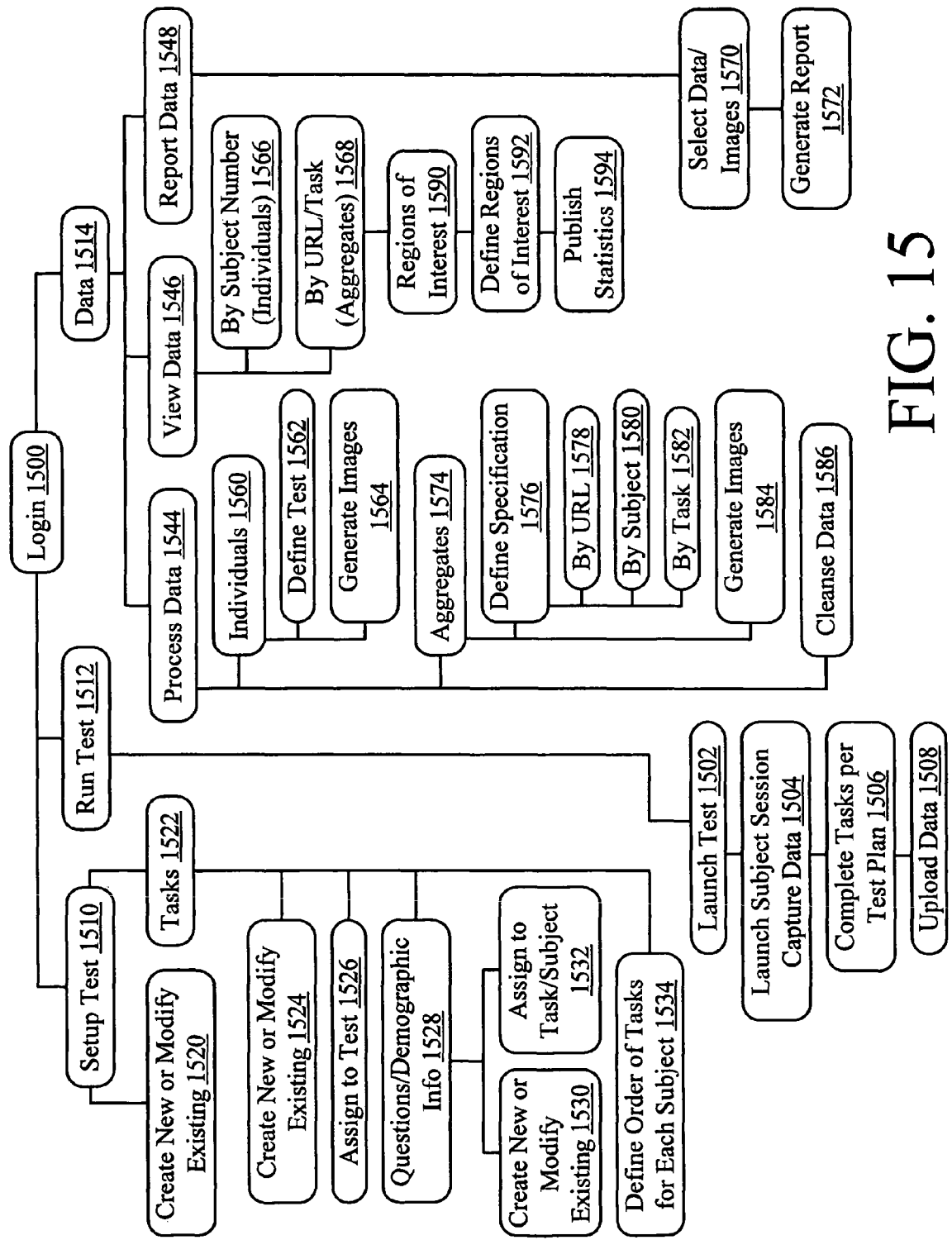
FIG. 15 is a hierarchical diagram of a design and testing structure for using eyetracking data.

FIG. 15 is a hierarchical diagram of a design and testing structure for using eyetracking data. A user or administrator may login to the system, 1500. Depending on privileges provided, the user may be provided with the option to setup a test (1510), run a test (1512) or examine data (1514).

If the user opts to setup a test, 1510, the user may be provided with the option to create a new test or to modify an existing test, 1520, which may include one or more tasks, 1522. In one embodiment, the task options may include, for example, the option to create new or modify existing tasks (1524), assign tasks to a test (1526), work with questions or demographic information (1528), and/or define the order of tasks for each subject (1534). In one embodiment, working with questions or demographic information, 1528, may include the option to create new or modify existing questions or demographic profiles (1530), and/or to assign questions or demographic profiles to a specific task or subject (1532).

If the user opts to run a test, 1512, the user may be provided with the option to launch a test (1502), launch a subject session to capture data (1504), complete tasks per a test plan (1506) and/or upload data (1508). If the user opts to work with the data, 1514, the user may be provided with the option to process data (1544), view data (1546) and/or report data (1548).

If the user opts to report data, 1548, the user may be provided with the ability to select data and/or images (1570) or to generate a report (1572). If the user opts to view the data, 1546, the user may be provided with the option to view data by individual participants (1566) or by groups (1568). When viewing the data, the user may also be provided with the option to work with regions of interest (1590), define regions of interest (1592) and/or publish statistics (1594).

If the user opts to process data, 1544, the data may be processed by individuals (1560), by for example, defining tests (1562) and/or generating images (1564). The data may also be processed for aggregates (1574) by defining specifications (1576) and/or generating images (1584). Specifications for the aggregate can be defined, for example, by URL (1578), by subjects (1580), or by task (1582). The user may also be provided with the option to cleanse the data (1586).

CONCLUSION

Reference in the specification to "one embodiment" or "an embodiment" means that a particular feature, structure, or characteristic described in connection with the embodiment is included in at least one embodiment of the invention. Use of the phrase "in one embodiment" in various places in the specification are not necessarily all referring to the same embodiment.

In the foregoing specification, the invention has been described with reference to specific embodiments thereof. It will, however, be evident that various modifications and changes can be made thereto without departing from the broader spirit and scope of the invention. The specification and drawings are, accordingly, to be regarded in an illustrative rather than a restrictive sense.

What is claimed is:

1. A method comprising:
   receiving, from an eye interpretation engine, at least an interpretation of eyetracking data corresponding to a plurality of users that are presented with a base interface having a base set of features;
   receiving external context data corresponding the interactions of the plurality of users with an application having the base interface, wherein the external context data is related to an operational state associated with a computing device running the application;
   determining a user familiarity with the base interface; and
   dynamically modifying a characteristic of a graphical user interface of the application based, at least in part, on the interpretation of the eyetracking data and the external context data by providing a simplified interface if a low level of familiarity is determined and by providing an enhanced set of features of a high level of familiarity is determined.

2. The method of claim 1 wherein dynamically modifying comprises one of: modifying, creating, destroying, removing, invoking and configuring.

3. The method of claim 1 wherein dynamically acting on a characteristic of the application based, at least in part, on the interpretation of the eyetracking data comprises:
   determining from the interpretation of the eyetracking data at least a portion of an interface that has not been viewed by one or more of the plurality of users;
   modifying a format of the portion of the interface that has not been viewed by one or more of the plurality of users.

4. A method comprising:
   receiving, from an eye interpretation engine, at least an interpretation of eyetracking data corresponding to a plurality of users that are presented with a base interface having a base set of features;
   receiving external context data corresponding the interactions of the plurality of users with an application having the base interface, wherein the external context data is related to an operational state associated with a computing device running the application;
   determining one or more areas that were skipped, skimmed and/or reread based on aggregated eyetracking data corresponding to the plurality of users;
   dynamically modifying a graphical output of the application displayed on an output device based, at least in part, on the interpretation of the eyetracking data and the external context data to compensate for the determined skipping, skimming and/or rereading.

5. The method of claim 4 wherein acting on comprises one of:
   modifying, creating, destroying, removing, invoking and configuring.

6. The method of claim 4 wherein dynamically acting on the output of the application based, at least in part, on the interpretation of the eyetracking data comprises:
   determining from the interpretation of the eyetracking data at least a portion of content that has not been viewed by one or more of the plurality of users;
   modifying a format of the portion of content that has not been viewed by one or more of the plurality of users.

7. An article comprising a non-transitory computer-readable medium having stored thereon instructions that, when executed, cause one or more processors to:
   receive, from an eye interpretation engine, at least an interpretation of eyetracking data corresponding to a plurality of users that are presented with a base interface having a base set of features;
   receive external context data corresponding the interactions of the plurality of users with an application having the base interface, wherein the external context data is related to an operational state associated with a computing device running the application;
   determine a user familiarity with the base interface; and
   dynamically modify a characteristic of a graphical user interface of the application based, at least in part, on the interpretation of the eyetracking data and the external context data by providing a simplified interface if a low level of familiarity is determined and by providing an enhanced set of features of a high level of familiarity is determined.

8. The article of claim 7 wherein dynamically modifying comprises one of: modifying, creating, destroying, removing, invoking and configuring.

9. The article of claim 7 wherein the instructions that cause the one or more processors to dynamically act on a characteristic of the application based, at least in part, on the interpretation of the eyetracking data comprise instructions that, when executed cause the one or more processors to:
   determine from the interpretation of the eyetracking data at least a portion of content that has not been viewed by one or more of the plurality of users;
   modify a format of the portion of the interface that has not been viewed by one or more of the plurality of users.

10. An article comprising a non-transitory computer-readable medium having stored thereon instructions that, when executed, cause one or more processors to:
    receive, from an eye interpretation engine, at least an interpretation of eyetracking data corresponding to a plurality of users that are presented with a base interface having a base set of features;
    receive external context data corresponding the interactions of the plurality of users with an application having the base interface, wherein the external context data is related to an operational state associated with a computing device running the application;
    determine one or more areas that were skipped, skimmed and/or reread based on aggregated eyetracking data corresponding to the plurality of users;
    dynamically modify a graphical output of the application displayed on an output device based, at least in part, on the interpretation of the eyetracking data and the external context data to compensate for the determined skipping, skimming and/or rereading.

11. The article of claim 10 wherein dynamically modify comprises one of: modifying, creating, destroying, removing, invoking and configuring.

12. The article of claim 10 wherein the instructions that cause the one or more processors to dynamically act on a characteristic of the application based, at least in part, on the interpretation of the eyetracking data comprise instructions that, when executed cause the one or more processors to:
    determine from the interpretation of the eyetracking data at least a portion of content that has not been viewed by one or more of the plurality of users;
    modify a format of the portion of the interface that has not been viewed by one or more of the plurality of users.

13. An article comprising a non-transitory computer—readable medium having stored thereon instructions that, when executed, cause one or more processors to:
    receive, from an eye interpretation engine, at least an interpretation of eyetracking data corresponding to a plurality of users that are presented with a base interface having a base set of features;
    receive external context data corresponding the at least interactions of the plurality of users with an application having the base interface, wherein the external context data is related to an operational state associated with a computing device running the application;
    determine a user familiarity with the base interface; and
    dynamically modify a graphical user interface the application based, at least in part, on the interpretation of the eyetracking data and the external context data.

14. The article of claim 13 wherein dynamically modify comprises one of: invoking, selecting, closing, creating and configuring.

15. The method of claim 1 wherein the external context data comprise one or more of: system information, location and/or z-order of windows and/or objects, Document Object Model (DOM) of a Web page or application being viewed, current application process state and/or visual state, task models, cognitive models describing the mental or physical steps or states required.

16. The method of claim 4 wherein the external context data comprise one or more of: system information, location and/or z-order of windows and/or objects, Document Object Model (DOM) of a Web page or application being viewed, current application process state and/or visual state, task models, cognitive models describing the mental or physical steps or states required.

17. The article of claim 7 wherein the external context data comprise one or more of: system information, location and/or z-order of windows and/or objects, Document Object Model (DOM) of a Web page or application being viewed, current application process state and/or visual state, task models, cognitive models describing the mental or physical steps or states required.

18. The article of claim 10 wherein the external context data comprise one or more of: system information, location and/or z-order of windows and/or objects, Document Object Model (DOM) of a Web page or application being viewed, current application process state and/or visual state, task models, cognitive models describing the mental or physical steps or states required.

19. The article of claim 13 wherein the external context data comprise one or more of: system information, location and/or z-order of windows and/or objects, Document Object Model (DOM) of a Web page or application being viewed, current application process state and/or visual state, task models, cognitive models describing the mental or physical steps or states required.

* * * * *